US005766256A

United States Patent [19]
Oudard et al.

[11] Patent Number: 5,766,256
[45] Date of Patent: Jun. 16, 1998

[54] TIBIAL PROSTHESIS

[75] Inventors: Jean-Loup Oudard, Saint-Nazaire les Eymes; Pierre Chambat, Sainte Foy les Lyons; Gérard Deschamps, Givry, all of France

[73] Assignee: Tornier SA, Saint-Ismier, France

[21] Appl. No.: 785,933

[22] Filed: Jan. 22, 1997

[30] Foreign Application Priority Data

Jan. 23, 1996 [FR] France .................................. 96 01012

[51] Int. Cl.[6] ............................................... A61F 2/38
[52] U.S. Cl. ............................................ 623/20; 623/18
[58] Field of Search ................................ 623/18, 20

[56] References Cited

U.S. PATENT DOCUMENTS 4,207,627  6/1980  Cloutier .
4,778,473  10/1988  Matthews et al. ................... 623/20
5,236,462  8/1993  Mikhail ................................ 623/20

FOREIGN PATENT DOCUMENTS

| 0001147 | 3/1979 | European Pat. Off. |
| 2654613 | 5/1991 | France ........................ 623/20 |
| 2700261 | 7/1994 | France ........................ 623/20 |
| 3136636 | 3/1983 | Germany . |

Primary Examiner—Randy C. Shay
Attorney, Agent, or Firm—Dowell & Dowell, P.C.

[57] ABSTRACT

A tibial prosthesis including a disk made out of a plastic material, of which a bottom surface is provided with fastening means for the interlocking with a metal ring which reinforces the disk.

19 Claims, 3 Drawing Sheets

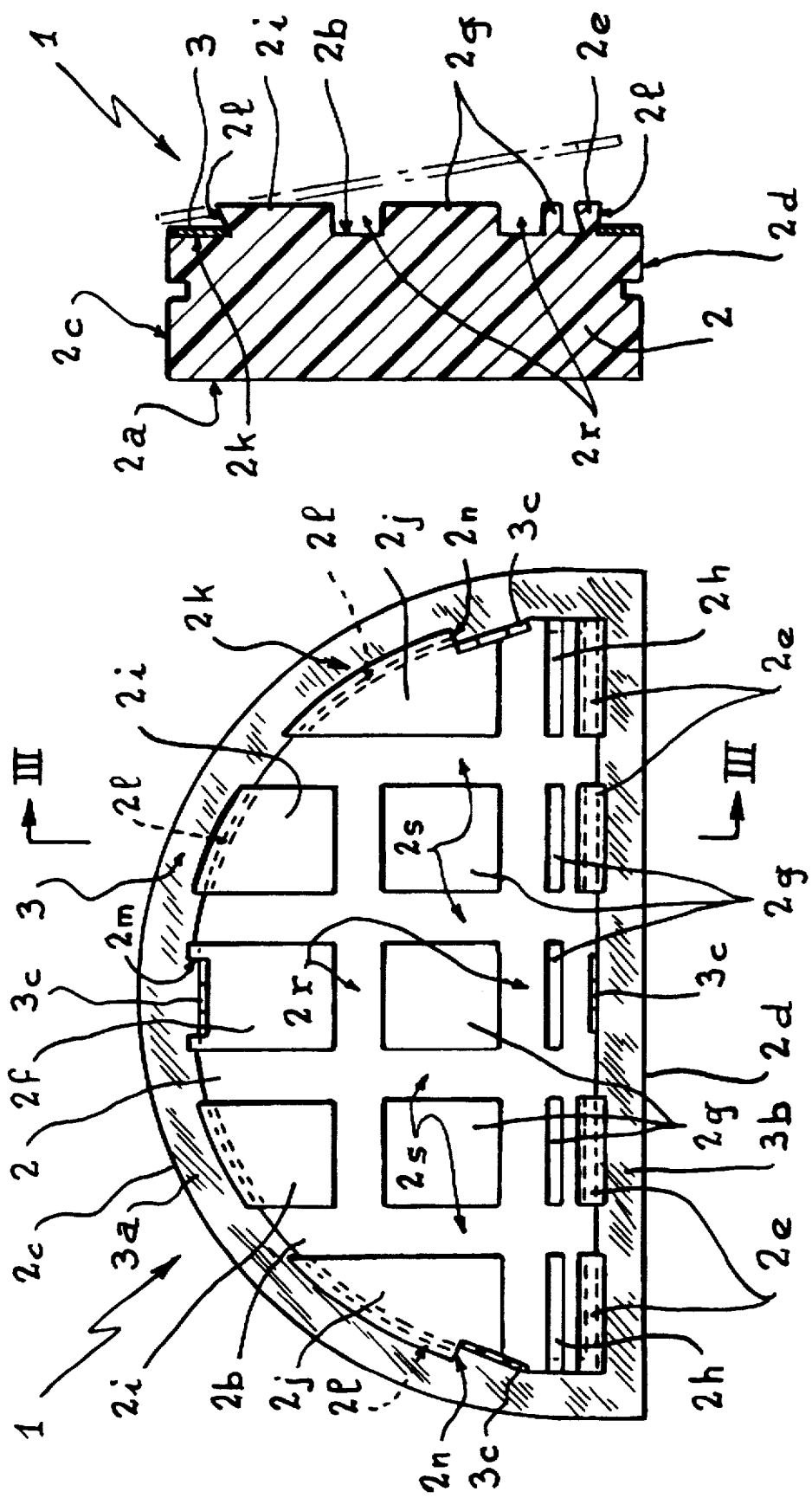

5,766,256

TIBIAL PROSTHESIS

BACKGROUND OF THE INVENTION

1. Field of the Invention

The present invention relates to a total or unicompartmentized tibial prosthesis provided with a disk out of a plastic material, bound along its periphery with a ring cut out from the plate or machined from the block.

2. History of the Related Art

Two types of disks are known for the manufacture of total or unicompartmentized tibial prostheses.

The first ones are manufactured from a large block of a plastic material but have the disadvantage of a low rigidness and poor creep resistance. Moreover, this type of disk precludes having resistant anchoring systems.

The second types, commonly called "metal back disks," are provided with a rigid metal seat, forming one piece or not, of an anchoring pin that penetrates into the medullar canal of a bone receiving the tibial prosthesis. This metal seat includes fastening means for affixing a thin plastic element of which one of its surfaces includes indentations to accommodate the condyles of the femur. This type of disk or plate, although rigid and having an adequate anchoring system, lacks longevity because of the thinness of the plastic material of the tibial element.

SUMMARY OF THE INVENTION

The purpose of the present invention is to remedy the foregoing disadvantages. The tibial prothesis in accordance with this invention comprises a plastic disk of which one of its surfaces is provided with fastening means to allow the interlocking of a metal ring which functions as a reinforcement of the prosthesis. Furthermore, the metal ring is provided with vertical teeth which extend toward the outside of the disk to facilitate the anchoring of the tibial prosthesis.

BRIEF DESCRIPTION OF THE DRAWINGS

By way of example, the accompanying drawing will allow a better understanding of the invention, of the characteristics it presents and of the advantages it is likely to bring.

FIG. 2 is a view from the underside of the tibial prosthesis showing the positioning of the metal ring on the disk.

FIG. 3 is a view along the line III—III of FIG. 2, showing the interlocking of the metal ring to the disk.

DESCRIPTION OF THE PREFERRED EMBODIMENT

Figure 1:
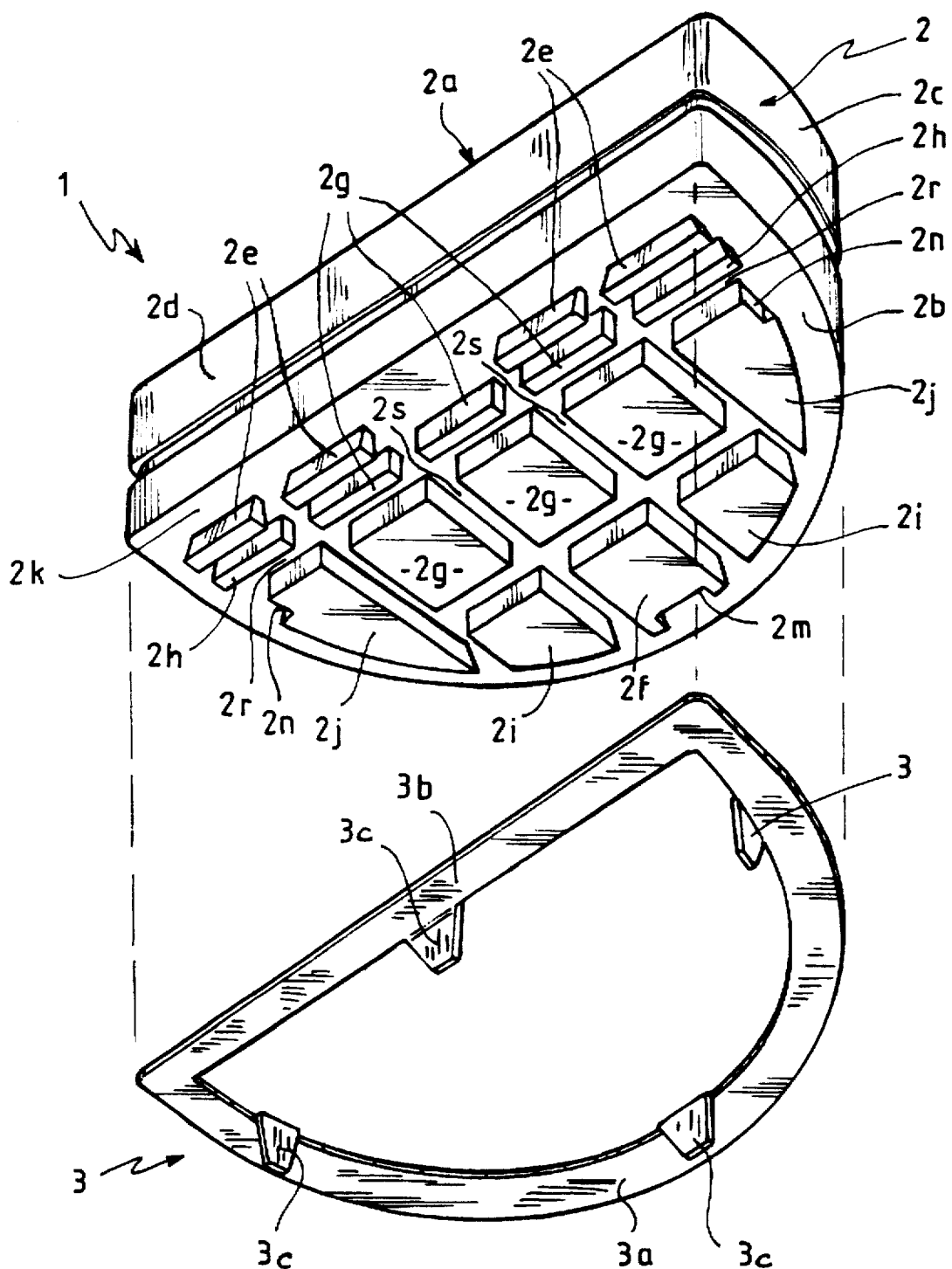
FIG. 1 is an assembly view showing the plastic disk and the metal ring of the tibial prosthesis in accordance with this invention.

FIGS. 1 to 3 show an unicompartmentized tibial prosthesis 1 provided with a disk 2 formed of a plastic material to which is affixed a metal ring 3 made out of a thin plate or a machined piece. The disk 2 has two opposing parallel upper and lower surfaces 2a and 2b, respectively of which the upper one has one or more indentations to accommodate the natural or prosthetic condyle(s) of the femur. In fact, the prosthesis 1 may be either total or unicompartmentized, depending on the surgical need.

The distance separating the two opposing parallel surfaces 2a and 2b is such that the maximum thickness of the plastic material is in the central portion of the disk 2. The disk 2 is shaped as a half-disk having a rim or peripheral edge 2c, either curved or of circular arc, that extends as a linear border 2d.

The surface 2b is provided with the fastening means for the interlocking of the metal ring 3 which functions as a reinforcement of the disk 2. By way of example, the fastening means are constituted by several raised studs 2e and 2j that are obtained from a machining of the surface 2b. The configuration and the disposition of the raised studs 2e to 2j can be modified; such a modification does not, however, change the object of the present invention.

It can be noted that the peripheral raised studs 2e, 2f, 2h, 2i and 2j are offset with respect to the rims 2c and 2d of disk 2 in order to constitute a flush or flat ring or seat 2k. The studs 2e are arranged parallel to the linear rim 2d while the studs 2f, 2i, and 2j are shaped in such a manner as to follow the curved rim 2c.

It can be observed that each of the peripheral studs 2e, 2f, 2h, 2i, and 2j has a slanted side 2l facing at an angle towards the seat or ring 2k. The peripheral studs 2e are somewhat elastic while the studs 2f, 2i and 2j are totally rigid in order to allow a perfect distribution of the stresses applied by the metal ring 3.

The studs 2f and 2j are provided with indentations 2m and 2n, respectively, facing towards the side of the ring 2k of the disk 2. The raised studs 2e to 2j are separated by horizontal grooves 2r and vertical grooves 2s of different width in order to allow cementing after the fastening of the prosthesis 1.

The shape of the metal ring 3 is similar to that of disk 2. The metal ring 3 has a curved or circular arc-shaped rim 3a that continues as a second linear rim 3b. The metal ring 3 is provided with vertical teeth 3c that are evenly distributed along the internal periphery of the rims 3a and 3b.

The vertical teeth 3c allow an improved anchoring of the tibial prosthesis 1 in two perpendicular directions with respect to the horizontal plane of the surface 2d of the disk 2.

It can be observed that the elastic deformation of the studs 2e allows the interlocking of the metal ring 3 in such a manner that the rims 3a and 3b are positioned on the ring 2k and at the slanted sides 2l of each peripheral stud 2e, 2f, 2h, 2i, and 2J in order to prevent any offsetting of the metal ring 3.

Figure 4:
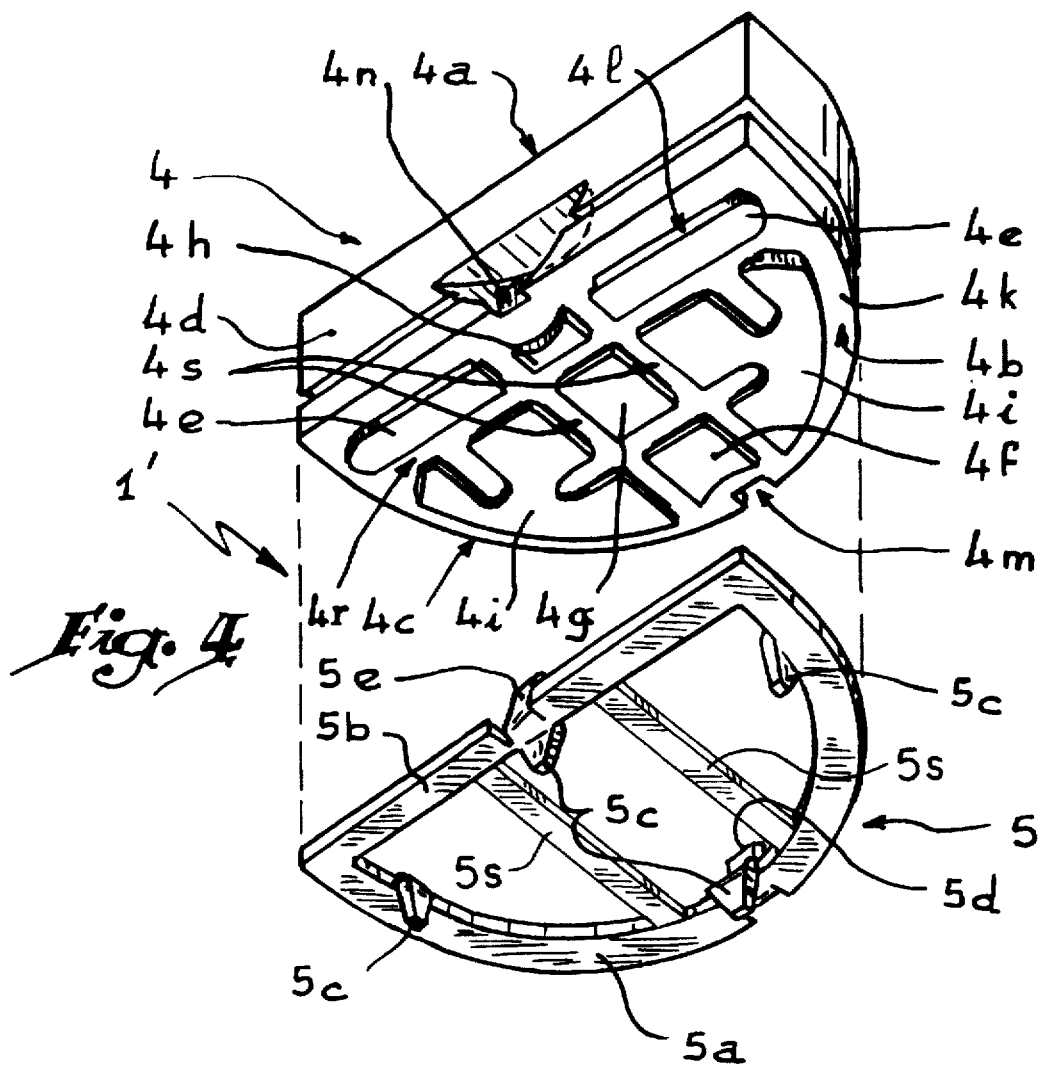
FIGS. 4 and 5 are views showing a variation of the interlocking of the metal ring to the disk.
Figure 5:
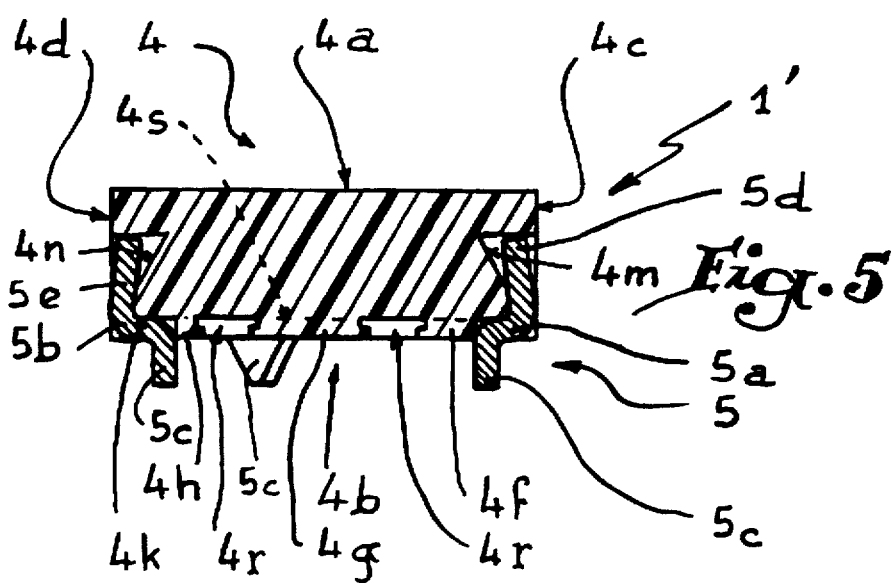

FIGS. 4 and 5 show a variation of the tibial prosthesis 1, denoted by numeral 1', provided with a disk 4 formed of a plastic material, to which is interlocked a thin metal ring 5 cut out from a plate or machined from a block. The disk 4 has two opposing parallel surfaces 4a and 4b, of which the upper one has one or more indentations to accommodate the natural or prosthetic condyle(s) of the femur. In fact, the prosthesis 1 may be either total or unicompartmentized, depending on the surgical need.

In the same manner as for the tibial prosthesis 1, the distance separating the two opposing parallel surfaces 4a and 4b is such that the maximum thickness of the plastic material is in the central portion of the disk 4. The disk 4 is shaped identical to the one of reference 2, that is as a half-disk having a rim 4c, either curved or of circular arc, that extends to a linear rim 2d.

The surface 4b is provided with the fastening means for a metal ring 5 which functions to reinforce the disk 4. By way of example, the fastening means are constituted by several raised studs 4e to 4i that are obtained from a machining of the surface 4b. The configuration and the disposition of the raised studs 4e to 4i can be modified; such a modification does not, however, change the object of the present invention.

It can be noted that the peripheral raised studs 4e, 4f, 4h, and 4i are offset with respect to the rims 4c and 4d of disk 4 in order to form a flush ring 4k. The studs 4e and 4h are arranged parallel to the rectilinear rim 4d while the studs 4f and 4i are shaped in such a manner as to follow the curved rim 4c.

It can be observed that each of the peripheral studs 4e and 4i has a slanted side 4l facing towards the side of the ring 4k. In certain cases the peripheral studs do not have a slanted side but rather a perpendicular side to the ring 4k. The curved rim 4c is provided with an indentation or recess 4m partly formed in the ring 4k on a level with the stud 4f. Likewise, the rectilinear rim 4d presents an indentation 4n opposite of 4m and partly opened in the ring 4k adjacent the stud 4h.

The raised studs 4e to 4j are separated by horizontal grooves 4r and vertical grooves 4s of different width in order to allow cementing after the fastening of the prosthesis 1'.

The shape of the metal ring 5 is similar to that of disk 4. The shape of the ring can be any shape provided that it assures a reinforcement of the disk 4. The metal ring 5 has a curved or circular arc-shaped rim 5a that continues as a second linear rim 5b.

The metal ring 5 is provided with vertical teeth 5c that are evenly distributed along the internal periphery of the rims 5a and 5b. The vertical teeth 5c allow an improved anchoring of the tibial prosthesis 1' in two perpendicular directions with respect to the horizontal plane of the surface 4d of the disk 4.

The rim 5a includes on its outer periphery and adjacent a tooth 5c another tooth 5d facing a direction opposite that of tooth 5c. Likewise, the linear rim 5b is provided with another tooth 5e at its outer periphery and adjacent the tooth 5c facing a direction opposite that of tooth 5c.

It can be observed that the elastic deformation of the teeth 5d and 5e allows the interlocking of the metal ring 5 in such a manner that the rims 5a and 5b are positioned on the ring 4k and against the sides 4l of each peripheral stud 4e and 2i in order to prevent any 15 offsetting or shifting of the metal ring 5. In fact, the teeth 5d and 5e extend into the indentations 4n and 4m, respectively, that are provided in the rims 4c and 4d of the disk 4.

The rims 3a, 5a, 3b, and 5b can be connected by two parallel strips 5s, as shown in FIG. 4, that would improve the rigidity and the positioning of the metal ring 3, 5. Should the metal ring 3, 5 be provided with parallel strips, these strips would fit within the grooves 2s, 4s (FIGS. 1 and 4, respectively provided for this purpose.

It goes without saying that this type of tibial prosthesis can be designed for unicompartmentized or total disks that accommodate the condyles of a natural or prosthetic femur. The configuration of the metal ring 3, 5 depends on the shape given to each raised stud 2e to 2j; 4e to 4i at the time the surface 2b, 4b is formed.

It must be further understood that the foregoing description was given only by way of example and that it does not limit at all the scope of the invention that would be respected even if the described details of manufacture would be replaced by any others similar.

What is claimed is:

1. A tibial prosthesis comprising, a disk formed of a plastic material and having an upper surface and a lower surface and a peripheral rim of a predetermined configuration, a metal ring for reinforcing said disk mounted to said lower surface adjacent said peripheral rim, fastening means extending outwardly from said lower surface for interlocking said metal ring with said disk, said metal ring being mounted to said disk between said fastening means and said peripheral rim.

2. The tibial prosthesis of claim 1, in which said fastening means includes a plurality of raised studs of which a number are elastically yieldable to interlock with said metal ring.

3. The tibial prosthesis of claim 2, wherein said plurality of raised studs includes peripheral studs which are positioned in spaced relationship with respect to said peripheral rim of said disk so that a portion of said lower surface between said peripheral studs and said peripheral rim define a flat seat surface upon which said metal ring is mounted.

4. The tibial prosthesis of claim 3, wherein each of said peripheral studs include a slanted side oriented toward said flat seat surface in order to interlock with said metal ring.

5. The tibial prosthesis of claim 4, wherein said metal ring includes a plurality of first teeth extending therefrom and away from said disk.

6. The tibial prosthesis of claim 5, wherein some of said peripheral studs have indentations open toward said peripheral rim in which said first teeth of said metal ring are cooperatively received.

7. The tibial prosthesis of claim 2, in which said plurality of raised studs have varying configurations.

8. The tibial prosthesis of claim 7, wherein said disk has a maximum thickness, measured between said upper and lower surfaces, at a central portion thereof.

9. The tibial prosthesis of claim 3, in which at least a portion of said peripheral rim is arcuate, some of said peripheral studs being adjacent said arcuate portion of said peripheral rim and including slanted sides which are arcuate and which face toward said arcuate portion of said peripheral rim.

10. The tibial prosthesis of claim 9, in which a portion of said peripheral rim is linear, some of said peripheral studs being adjacent said linear portion of said rim and having slanted sides which are oriented towards said linear portion of said peripheral rim.

11. The tibial prosthesis of claim 1, in which said fastening means includes a plurality of elastically yieldable raised studs, said metal ring including first and second oppositely oriented teeth, said second teeth extending toward said disk and being received in indentations formed in said disk.

12. The tibial prosthesis of claim 1, wherein said metal ring is formed of a thin plate that includes a curved ring portion that extends to opposite ends of a linear ring portion.

13. The tibial prosthesis of claim 12, wherein said curved and linear portions of said metal ring are connected by metal strips that rigidify said metal ring.

14. A tibial prosthesis comprising, a disk formed of a plastic material and having an upper surface and a lower surface and a peripheral rim of a predetermined configuration, a metal ring for reinforcing said disk mounted to said lower surface adjacent said peripheral rim, said lower surface including fastening means for interlocking with said metal ring, and said metal ring including teeth that interlock with said disk.

15. The tibial prosthesis of claim 14, including first teeth oriented away from said disk and second teeth extending toward said disk.

16. A tibial prosthesis comprising, a disk formed of a plastic material and having an upper surface and a lower surface and a peripheral rim of a predetermined configuration, a metal ring for reinforcing said disk mounted to said lower surface adjacent said peripheral rim, said lower surface including fastening means for interlocking with said metal ring, which metal ring reinforces the disk, and said metal ring being formed of a thin plate that includes a curved ring portion that extends to opposite ends of a linear ring portion, wherein said curved and linear portions of said metal ring are connected by metal strips that rigidify said metal ring.

17. The tibial prosthesis of claim 16 wherein said fastening means includes a plurality of first raised studs extending from said lower surface and engaging said metal ring, said plurality of first raised studs being elastically yieldable.

18. The tibial prosthesis of claim 18 wherein said fastening means also includes a plurality of second raised studs spaced from said plurality of first raised studs and engaging said metal ring.

19. The tibial prosthesis of claim 18 wherein said plurality of second raised studs are rigid, and said metal ring being mounted to said lower surface so as to apply stress to said plurality of said first and second raised studs one another.

* * * * *